(12) United States Patent
Hunter et al.

(10) Patent No.: US 6,852,336 B2
(45) Date of Patent: *Feb. 8, 2005

(54) DIRECTLY COMPRESSIBLE HIGH LOAD ACETAMINOPHEN FORMULATIONS

(75) Inventors: Edward A. Hunter, Glenham, NY (US); Bob E. Sherwood, Amenian, NY (US); Joseph A. Zeleznik, New Paltz, NY (US)

(73) Assignee: J. Rettenmaier & Soehne GmbH + Co. KG, Rosenberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/113,867

(22) Filed: Apr. 1, 2002

(65) Prior Publication Data

US 2002/0197310 A1 Dec. 26, 2002

Related U.S. Application Data

(60) Continuation of application No. 09/798,755, filed on Mar. 2, 2001, now Pat. No. 6,391,337, which is a continuation of application No. 09/311,210, filed on May 13, 1999, now Pat. No. 6,217,907, which is a continuation of application No. 08/964,917, filed on Nov. 5, 1997, now Pat. No. 5,965,166, which is a division of application No. 08/558,335, filed on Nov. 15, 1995, now Pat. No. 5,733,578.

(51) Int. Cl.[7] .............................. A61K 9/14; A61K 9/16; A61K 9/20; A61K 9/28
(52) U.S. Cl. ...................... 424/489; 424/490; 424/497; 424/464; 424/465; 424/474
(58) Field of Search ............................. 424/474, 489, 424/490, 464, 465, 497

(56) References Cited

U.S. PATENT DOCUMENTS 3,023,104 A 2/1962 Battista et al. .................. 99/1
3,067,037 A 12/1962 Herald et al. .................. 99/139

(List continued on next page.)

FOREIGN PATENT DOCUMENTS

| CA | 1261261 | 9/1989 | ............ A61K/9/20 |
| DE | 4303846 | 8/1994 | .......... A61K/31/19 |

(List continued on next page.)

OTHER PUBLICATIONS

Machines Collette High Shear Mixer Granulator Promotional Literature (date unknown).

*Primary Examiner*—Thurman K. Page
*Assistant Examiner*—Humera N. Sheikh
(74) *Attorney, Agent, or Firm*—Davidson, Davidson & Kappel

(57) ABSTRACT

Direct compressed solid pharmaceutical dosage forms containing:
  a) from about 40 to about 95% by weight acetaminophen;
  b) from about 1 to about 60% by weight of a direct compression vehicle comprising microcrystalline cellulose; and
  c) from about 0.01 to about 4.0% by weight of a pharmaceutically-acceptable lubricant are disclosed. The acetaminophen and direct compression vehicle are combined under high shear conditions which are sufficient to transform acetaminophen and direct compression vehicle into a homogenous granulate without degradation. In preferred aspects of the invention, the lubricant is also combined with the acetaminophen and direct compression vehicle under high shear conditions. Methods of preparing the directly compressed solid pharmaceutical dosage forms and methods of treatment with the dosage forms are also disclosed. The methods are particularly well suited for preparing directly compressed dosage forms containing high load (i.e., up to 80% or greater) amounts of acetaminophen based on the weight of the total tablet.

49 Claims, 3 Drawing Sheets

U.S. PATENT DOCUMENTS

| | | | |
|---|---|---|---|
| 3,141,875 A | 7/1964 | Battista | 260/212 |
| 3,539,365 A | 11/1970 | Durand et al. | 106/197 |
| 3,573,058 A | 3/1971 | Tiemstra | 99/1 |
| 4,109,018 A | 8/1978 | Thompson | 426/62 |
| 4,143,163 A | 3/1979 | Hutchison et al. | 426/96 |
| 4,156,021 A | 5/1979 | Richardson | 426/104 |
| 4,159,345 A | 6/1979 | Talep | 424/352 |
| 4,219,580 A | 8/1980 | Torres | 426/549 |
| 4,232,052 A | 11/1980 | Nappen | 426/601 |
| 4,439,453 A | 3/1984 | Vogel | |
| 4,505,862 A | 3/1985 | Sheinaus et al. | 260/501.18 |
| 4,533,674 A | 8/1985 | Schmidt et al. | |
| 4,631,284 A | 12/1986 | Salpekar et al. | |
| 4,664,915 A | 5/1987 | Simonian | 424/128 |
| 4,744,987 A | 5/1988 | Mehra et al. | 424/156 |
| 4,748,027 A | 5/1988 | Schou et al. | 426/96 |
| 4,814,195 A | 3/1989 | Yokoyama et al. | 426/633 |
| 4,911,946 A | 3/1990 | Singer et al. | 426/658 |
| 4,946,685 A | 8/1990 | Edgren et al. | 424/472 |
| 4,980,193 A | 12/1990 | Tuason, Jr. et al. | 426/654 |
| 5,011,701 A | 4/1991 | Baer et al. | 426/573 |
| 5,026,569 A | 6/1991 | Forand | 426/549 |
| 5,030,400 A | 7/1991 | Danielson et al. | 264/101 |
| 5,075,115 A | 12/1991 | Brine | 424/486 |
| 5,126,145 A | 6/1992 | Evenstadt et al. | 424/465 |
| 5,132,128 A | 7/1992 | Rockland | 426/658 |
| 5,158,798 A | 10/1992 | Fung et al. | 426/602 |
| 5,192,569 A | 3/1993 | McGinley et al. | 426/96 |
| 5,209,942 A | 5/1993 | Bauer et al. | 426/573 |
| H1229 H | 9/1993 | McGinley et al. | 426/654 |
| 5,322,698 A | 6/1994 | Kovacs et al. | 424/480 |
| 5,338,562 A | 8/1994 | Humphreys | 426/603 |
| 5,366,742 A | 11/1994 | Tuason, Jr. et al. | 426/96 |
| 5,370,878 A | 12/1994 | Shah | 424/469 |
| 5,429,830 A | 7/1995 | Janovsky et al. | 426/94 |
| 5,441,753 A | 8/1995 | McGinley et al. | 426/96 |
| 5,462,761 A | 10/1995 | McGinley et al. | 426/573 |
| 5,505,982 A | 4/1996 | Krawczyk et al. | 426/660 |
| 5,560,926 A | 10/1996 | Franz et al. | |
| 5,585,115 A | 12/1996 | Sherwood et al. | |
| 5,733,578 A | 3/1998 | Hunter et al. | |
| 5,965,166 A | 10/1999 | Hunter et al. | |
| 6,217,907 B1 | 4/2001 | Hunter et al. | |

FOREIGN PATENT DOCUMENTS

| | | | |
|---|---|---|---|
| EP | 0305051 | 3/1989 | A61K/9/22 |
| EP | 0430287 | 6/1991 | A61K/9/52 |
| EP | 0543541 | 5/1993 | A61K/31/165 |
| EP | 0609976 | 9/1994 | |
| GB | 1464200 | 2/1977 | A61K/31/505 |
| GB | 1480188 | 7/1977 | A61K/9/16 |
| WO | 9014017 | 11/1990 | A23L/1/0534 |
| WO | WO 92/03126 | 3/1992 | A61K/9/20 |
| WO | 9212633 | 8/1992 | A01N/25/10 |
| WO | 9312768 | 7/1993 | A61K/9/14 |
| WO | 9406309 | 3/1994 | A23L/1/38 |
| WO | 9520326 | 8/1995 | A23L/1/0534 |
| WO | WO 9535104 | 12/1995 | A61K/31/19 |

DIRECTLY COMPRESSIBLE HIGH LOAD ACETAMINOPHEN FORMULATIONS

This application is a continuation application of U.S. Ser. No. 09/798,755, filed Mar. 2, 2001 now U.S. Pat. No. 6,391,337, which is a continuation of U.S. Ser. No. 09/311,210, filed May 13, 1999, now U.S. Pat. No. 6,217,907, which in turn is a continuation of U.S. Ser. No. 08/964,917, filed Nov. 5, 1997, now U.S. Pat. No. 5,965,166, which in turn is a divisional of U.S. Ser. No. 08/558,335, filed Nov. 15, 1995, now U.S. Pat. No. 5,733,578.

BACKGROUND OF THE INVENTION

The present invention relates to methods of preparing solid dosage forms using direct compression techniques. In particular, the present invention relates to methods of directly compressing tablets containing relatively high amounts of acetaminophen based on the total tablet weight.

In order to prepare a solid dosage form containing one or more active ingredients (such as drugs), it is necessary for the materials to be compressed into the dosage form possess certain physical characteristics which lend themselves to solid dosage form processing. Among other things, the material to be compressed must be free-flowing, must be lubricated, and, importantly, must possess sufficient cohesiveness to insure that the solid dosage form remains intact after compression.

In the case of tablets, the tablet is formed by pressure being applied to the material to be tabletted on a tablet press. A tablet press includes a lower punch which fits into a die from the bottom and a upper punch having a corresponding shape and dimension which enters the die cavity from the top after the tabletting material fills the die cavity. The tablet is formed by pressure applied on the lower and upper punches. The ability of the material to flow freely into the die is important in order to insure that there is a uniform filling of the die and a continuous movement of the material from the source of the material, e.g. a feeder hopper. The lubricity of the material is crucial in the preparation of the solid dosage forms since the compressed material must be readily ejected from the punch faces.

Since most drugs have none or only some of these properties, methods of tablet formulating have been developed to impart these desirable characteristics to the material(s) which is to be compressed into a solid dosage form. Typically, excipients are added to the formulation which impart good flow and compression characteristics to the material as a whole which is to be compressed. Such properties are typically imparted to these excipients via a pre-processing step such as wet granulation, slugging, spray drying, spheronization, or crystallization. Useful direct compression excipients include processed forms of cellulose, sugars, and dicalcium phosphate dihydrate, among others.

Lubricants are typically added to avoid the material(s) being tabletted from sticking to the punches. Commonly used lubricants include magnesium stearate and calcium stearate. Such lubricants are commonly included in the final tabletted product in amounts usually less than 1% by weight.

In addition, solid dosage forms often contain diluents. Diluents are frequently added in order to increase the bulk weight of the material to be tabletted in order to make the tablet a practical size for compression. This is often necessary where the dose of the drug is relatively small.

Another commonly used class of excipients in solid dosage forms are binders. Binders are agents which impart cohesive qualities to the powdered material(s). Commonly used binders include starch, and sugars such as sucrose, glucose, dextrose, and lactose.

Disintegrants are often included in order to ensure that the ultimately prepared compressed solid dosage form has an acceptable disintegration rate in an environment of use (such as the gastrointestinal tract). Typical disintegrants include starch derivatives and salts of carboxymethylcellulose.

There are three general methods of preparing the materials to be included in the solid dosage form prior to compression: (1) dry granulation; (2) wet granulation; and (3) direct compression.

Dry granulation procedures may be utilized where one of the constituents, either the drug or the diluent, has sufficient cohesive properties to be tabletted. The method includes mixing the ingredients with a lubricant, if required, slugging the ingredients, dry screening, lubricating and finally compressing the ingredients.

The wet granulation procedure includes mixing the powders to be incorporated into the dosage form in, e.g., a twin shell blender or double-cone blender under shear mixing conditions and thereafter adding solutions of a binding agent to the mixed powders to obtain a granulation. Thereafter, the damp mass is screened, e.g., in a 6- or 8-mesh screen and then dried, e.g., via tray drying or fluid-bed drying. The wet granulating technique is rather time consuming due to its process steps and can also be considered to be relatively expensive. In addition, wet granulating has been known to reduce the compressibility of some pharmaceutical ingredients including microcrystalline cellulose.

Direct compression, on the other hand, is regarded as a relatively quick process wherein the powdered materials included in the solid dosage form are compressed directly without modifying their physical nature usually, the active ingredient, direct compression vehicle and other ancillary substances, such as a glidant to improve the rate of flow of the tablet granulation and lubricant to prevent adhesion of the tablet material to the surface of the dies and punches of the tablet press, are blended in a twin shell blender or similar low shear apparatus before being compressed into tablets. This type of mixing of the ingredients was believed to be essential in order to prepare pharmaceutically acceptable dosage forms. For example, *Remington's Pharmaceutical Sciences*, 16th Edition (1980), Arthur Osol, Ed., cautions artisans that the manner in which a lubricant is added to a formulation must be carefully controlled. Consequently, lubricants are usually added to a granulation by gentle mixing. At page, 1556, *Remington's*, warns: "Prolonged blending of a lubricant with a granulation can materially affect the hardness and disintegration time for the resulting tablets." Further, those of ordinary skill in the art have long believed that excessive mixing of a lubricant with the granulate ingredients overcoats the granules and reduces the tablet hardness or tablet strength of the compressed tablets. Thus, for at least these reasons, high shear mixing conditions have not been used to prepare direct compression dosage forms.

Pharmaceutical manufacturers would often prefer to use direct compression techniques over wet or dry granulation techniques because of its processing time and cost advantages. Direct compression, however, is usually limited to those situations where the drug or active ingredient has a requisite crystalline structure and the physical characteristics required for formation of a pharmaceutically acceptable tablet. Often, however, one or more excipients must be combined with the active ingredient before the direct compression method can be used since many active ingredients do not have the necessary properties. Since each excipient added to formulation necessarily increases the tablet size of the final product, artisans were often limited to using direct compression techniques in formulations containing a rather low load of active ingredient per compressed tablet. Solid dosage forms containing the drug to be administered in a relatively high load or dose (e.g., the drug itself comprises a substantial portion of the total compressed tablet weight), could only be directly compressed if the drug itself had sufficient physical characteristics (e.g., cohesiveness) for the ingredients to be directly compressed.

For example, acetaminophen, a widely used analgesic, is considered to be a high load active ingredient. Most commercial compressed tablet formulations include anywhere from 70 to 85% by weight acetaminophen per finished tablet. This high load of active ingredient combined with its rather poor physical characteristics for direct compression have not allowed pharmaceutical manufacturers to use direct compression techniques to prepare the final tablets. Previous attempts to directly compress acetaminophen with microcrystalline cellulose have failed to provide an acceptable product. The final products tend to be soft, prone to capping and otherwise not commercially desirable, i.e., difficult to swallow because of the large size. Consequently, the more time consuming and expensive wet granulation techniques must be used.

Thus, another limitation of direct compression as a method of tablet manufacturing is the potential size of the compressed tablet. If the amount of active ingredient is high, a pharmaceutical formulator may choose to wet granulate the active with other excipients to attain an acceptably sized tablet with the desired amount of acetaminophen. Usually the amount of filler/binder or excipients needed in wet granulation is less than that required for direct compression since the process of wet granulation contributes to some extent toward the desired physical properties of a tablet.

Microcrystalline cellulose, a processed cellulose, has been utilized extensively in the pharmaceutical industry as a direct compression vehicle for solid dosage forms. Microcrystalline cellulose is commercially available under the tradename EMCOCEL® from Edward Mendell Co., Inc. and as Avicel® from FMC Corp. Compared to other directly compressible excipients, microcrystalline cellulose is generally considered to exhibit superior compressibility and disintegration properties as long as it is not wet granulated prior to compression.

Thus, despite the advantages of direct compression such as reduced processing times and costs, wet granulation is widely used in the industry to prepare solid dosage forms. Currently, many skilled in the art also prefer wet granulation over direct compression because wet granulating has a greater probability of overcoming any problems associated with the physical characteristics of the various ingredients in the formulation, thereby providing a material which has the requisite flow and cohesive characteristics necessary to obtain an acceptable solid dosage form.

The popularity of the wet granulation process as compared to the direct compression process is based on at least three advantages. First, wet granulation provides the material to be compressed with better wetting properties, particularly in the case of hydrophobic drug substances. The addition of a hydrophilic excipient makes the surface of a hydrophobic drug more hydrophilic, easing disintegration and dissolution. Second, the content uniformity of the solid dosage forms is generally improved with the wet granulation method because all of the granules obtained thereby usually contain approximately the same amount of drug. Thus, segregation of the different ingredients of the material to be compressed (due to different physical characteristics such as density) is avoided. Segregation is a potential problem with the direct compression method. Finally, the particle size and shape of the particles comprising the granulate to be compressed are optimized via the wet granulation process. This is due to the fact that when a dry solid is wet granulated, the binder "glues" particles together, so that they agglomerate in the granules which are more or less spherical.

In spite of the advantages afforded by wet granulation methods, many manufacturers would nonetheless welcome the opportunity to directly compress tablets containing acetaminophen, especially those containing high loads of acetaminophen and/or microcrystalline cellulose.

Thus, there still remains a need in the industry for techniques and pharmaceutical excipients which would allow artisans to prepare direct compressed dosage forms containing relatively high amounts of acetaminophen by weight and thereby avoid the time and expense of wet granulations.

OBJECTS AND SUMMARY OF THE INVENTION

It is an object of the present invention to provide improvements in direct compression techniques.

It is a further object of the present invention to provide a cost effective alternative to wet granulating acetaminophen formulations in order to prepare solid dosage forms containing a relatively high proportion of the drug when compared to the total weight of the dosage form.

It is a further object of the present invention to provide direct compressed acetaminophen oral solid dosage forms which disintegrate rapidly in vivo and in vitro.

A further object of the present invention is to provide direct compressed dosage forms which provide controlled release of acetaminophen without relying on fluidized bed or wet granulating techniques.

Another object of the present invention is to provide solid dosage forms which include acetaminophen and which are prepared according to the methods described herein.

In accordance with the above objects and others which will be obvious to those skilled in the art, the present invention includes a direct compressed solid pharmaceutical dosage form containing:

a) from about 40 to about 95% by weight acetaminophen;

b) from about 1 to about 60% by weight of a direct compression vehicle comprising microcrystalline cellulose; and c) from about 0.01 to about 4.0% by weight of a pharmaceutically-acceptable lubricant.

The acetaminophen and direct compression vehicle included in the direct compressed dosage form are combined under shear mixing conditions which are sufficient to transform the acetaminophen and direct compression vehicle into a homogenous granulate without degradation.

In preferred embodiments of this aspect of the invention, the solid dosage form comprises from about 60% to about 85% by weight acetaminophen and the acetaminophen is in granular form. The solid dosage forms accordingly can contain from about 10 to about 1000 milligrams of acetaminophen. In a particularly preferred embodiment, the direct compression vehicle includes microcrystalline cellulose which has been coprocessed with from about 0.1 to about 20% by weight silicon dioxide so that the microcrystalline cellulose and silicon dioxide are in intimate association with each other and provide enhanced compressibility properties for the direct compressed dosage forms. An additional preferred embodiment includes preparing the direct compressed solid pharmaceutical dosage form to include from about 0.1 to about 1% by weight of a pharmaceutically acceptable lubricant such as sodium stearyl fumarate. The lubricant is included as part of the homogeneous mixture containing the acetaminophen and direct compression vehicle and is preferably admixed with these ingredients under the same or similar high shear conditions used to form the homogeneous mixture.

In another embodiment, the direct compressed dosage forms of the present invention include from about 0.1 to about 5.0% by weight silicon dioxide. The silicon dioxide is preferably combined with the homogeneous mixture containing the acetaminophen and direct compression vehicle during the same high shear mixing conditions used to transform the ingredients into the homogeneous mixture.

In another embodiment of the invention, the direct compressed dosage forms include a disintegrant which has preferably been high shear mixed with the aforementioned acetaminophen, direct compression vehicle and lubricant.

One particularly preferred solid dosage form of the present invention includes at least about 75% by weight acetaminophen and has an average tablet hardness of about 6.5 kP when the homogeneous granulate containing the acetaminophen and microcrystalline cellulose is direct compressed at a compression force of about 25 kN.

The tablets of the present invention also have a relatively rapid disintegration rate which compares favorably with acetaminophen tablets prepared using wet granulation techniques. In certain preferred embodiments, the disintegration rate for the tablets of the present invention meets the requirements set forth in the USP 23© 1994 United States Pharmacopeial Convention, Inc. Furthermore, the dissolution rate of the inventive tablets is also believed to compare favorably, and in certain embodiments, even exceed that of wet granulated APAP products. In certain preferred embodiments, the inventive tablets also meet the dissolution requirements for acetaminophen tablets as set forth in the USP 23 official monograph. For example, the direct compressed APAP tablets will preferably dissolve in 900 ml of pH 5.8 phosphate buffer in 30 minutes. The "dissolution requirements" and "disintegration requirements" referred to herein are conducted using the equipment and tests specified in the aforementioned USP 23.

In another aspect of the present invention, there are provided methods of preparing direct compressed solid pharmaceutical dosage forms containing acetaminophen. This aspect of the invention includes first combining an effective amount of acetaminophen and a direct compression vehicle which comprises microcrystalline cellulose under shear conditions which are sufficient to transform the acetaminophen and direct compression vehicle into a first homogenous granulate without degradation. Next, the homogeneous granulate is combined with a pharmaceutically-acceptable lubricant, either by similar high shear or other dry mixing conditions, and thereafter compressing the resultant homogenous granulate containing the lubricant into solid pharmaceutical dosage forms.

Alternative aspects of the inventive methods described herein include forming a high shear mixture which includes silicon dioxide, preferably in the form of colloidal silicon dioxide. One particularly preferred method includes forming a first high shear mixture containing acetaminophen and a direct compression vehicle which includes microcrystalline cellulose and silicon dioxide before adding the lubricant under high shear conditions.

A still further aspect of the inventive method includes preparing direct compression solid pharmaceutical dosage forms by preparing a first high shear mixture by combining the acetaminophen, direct compression vehicle and, optional silicon dioxide and/or disintegrant. Next, the first high shear mixture is combined with a lubricant in a separate shear mixing step to form the final homogenous granulate. In this aspect of the invention, however, the second shear mixing step is carried out under conditions which are milder than those used to carry out the first shear mixing step.

For purposes of the present invention, the term "high-load" is meant to indicate that the acetaminophen comprises a substantial portion of the solid oral dosage form on a weight basis. Those of ordinary skill in the art recognize that compressed tablets containing at least about 40% by weight of acetaminophen are "high-load" tablets.

The term "granular" for purposes of the present invention is meant to connote particles having an average cross-sectional diameter of from about 50 to about 500 microns. The granular particles are to be distinguished from powdered particles having a particle size of less than about 50 microns and more likely in the range of 10–20 microns.

The term "environmental fluid" is meant for purposes of the invention to encompass, e.g., an aqueous solution, or gastrointestinal fluid.

"Sustained release" is meant for purposes of the invention to mean that the acetaminophen is released from the solid dosage form at a controlled rate such that therapeutically beneficial blood levels (but below toxic levels) of the active ingredient are maintained over an extended period of time, e.g., providing a 12 hour or a 24 hour dosage form.

"Controlled release" is meant for purposes of the invention to mean that the acetaminophen is released from the solid dosage form at a predetermined rate such that therapeutically beneficial blood levels are maintained over a period of time.

By "bioavailable" it is meant for purposes of the invention that the acetaminophen is absorbed from the dosage form and becomes available in the body at the intended site of action.

By "primary particle size" it is meant for purposes of the invention that the particles are not agglomerated. Agglomeration is common with respect to silicon dioxide particles, resulting in a comparatively average large agglomerated particle size.

The methods and compositions of the present invention provide several advantages to pharmaceutical formulators with regard to direct compression techniques. For example, the methods provide artisans with the ability to include high-load amounts of acetaminophen in direct compression dosage forms. In the past, high-load oral solid dosage forms containing acetaminophen could only be prepared using wet granulation techniques because the amount of additional excipients required to impart the necessary physical characteristics, such as hardness and size, rendered the final dosage forms unacceptable for both manufacturers and consumers.

A further advantage of the present invention is that it is now possible to increase the tablet hardness of acetaminophen-containing solid dosage forms by subjecting the formulation to high shear blending. This technique is especially advantageous in situations where one or more of the formulation ingredients, such as an additional active ingredient, is incapable of undergoing wet granulation.

For a better understanding of the present invention, together with other and further objects, reference is made to the following description, taken together with the accompanying figures, and the scope of the invention will be pointed out in the appended claims.

BRIEF DESCRIPTION OF THE DRAWINGS

The following drawings are illustrative of embodiments of the invention and are not meant to limit the scope of the invention as encompassed by the claims.

DETAILED DESCRIPTION OF THE INVENTION

Figure 1:
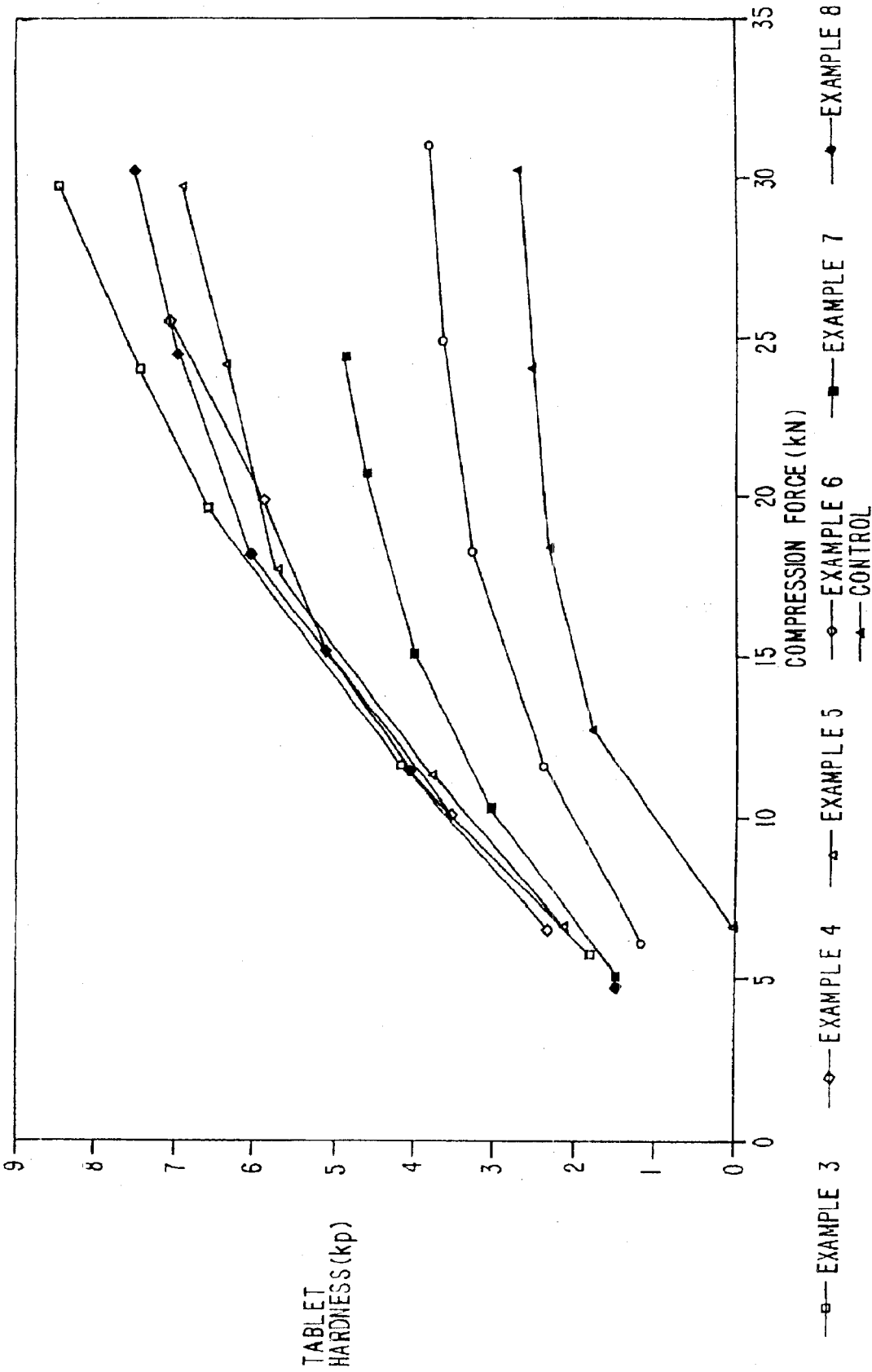
FIG. 1 graphically illustrates the tensile strengths of high load APAP tablets prepared in accordance with Examples 3–5, 7, 8, a control high load APAP tablets made in accordance with Example 6 and a second control prepared using prior art techniques.

In one aspect of the invention, there are provided direct compressed solid pharmaceutical dosage forms comprising:

a) from about 40 to about 95% by weight acetaminophen;

b) from about 1 to about 60% by weight of a direct compression vehicle comprising microcrystalline cellulose; and c) from about 0.01 to about 4.0% by weight of a pharmaceutically-acceptable lubricant. The acetaminophen and direct compression vehicle are combined under shear mixing conditions which are sufficient to transform the acetaminophen and direct compression vehicle into a homogenous granulate without degradation. The lubricant included in the dosage forms is also combined with the homogeneous granulate. In this regard, high shear conditions are preferred although not required.

Acetaminophen

The acetaminophen, hereinafter APAP, used in the direct compressed dosage forms of the present invention is preferably in granular form and has an average cross-sectional diameter of from about 50 to about 500 microns. More preferably, however, the granular APAP has a cross sectional diameter of from about 250–300 microns. Acetaminophen having these physical characteristics is available, for example from Mallinkrodt, St. Louis, Mo. USA. An alternative acetaminophen, also available from Mallinkrodt is DC-90. It is to be understood that the present invention is not limited to these types of granular APAP. Other sources of APAP are also contemplated so long as the APAP has the granular characteristics set forth above.

The granular APAP preferably used in the dosage forms of the present invention is to be contrasted with powdered forms of the active ingredient. Such powdered forms of APAP have a cross sectional diameter of from about 10–20 microns and are not contemplated for use herein. While applicants are not bound by theory, it is believed that a critical particle size is required to successfully withstand the high shear mixing conditions which transform the APAP, in high load amounts, and direct compression vehicle into a flowable granulate which is capable of being direct compressed into solid dosage forms having sufficient hardness and other physical qualities associated with an acceptable dosage form.

In a preferred aspect of the invention, the solid dosage forms contain from about 60 to about 85% by weight acetaminophen. Of course, the exact amount of acetaminophen included in the dosage forms of the present invention will depend upon the size of tablet and dosage amount contemplated by the artisan. Currently, APAP tablets are frequently formulated to contain from about 160 to about 650 milligrams of the drug. Tablets containing about 325 and about 500 milligrams are also commonly found. Several other APAP formulations are also commercially available. The tablets of the present invention contain from about 10 to about 1000 milligrams of APAP, preferably from about 80 to about 750 milligrams of APAP and most preferably from about 120 to about 650 milligrams of APAP.

In an alternative aspect of the invention the direct compressed acetaminophen tablets are prepared to contain an additional active ingredient such as those commonly found in APAP products. A non-limiting list of suitable ingredients which may be combined with the APAP includes narcotic analgesics such as codeine phosphate, oxycodone and hydromorphone, sinus and/or nasal decongestant ingredients such pseudoephedrine and antihistamines such as diphenhydramine.

Direct Compression Vehicles

The direct compression vehicles used in the solid dosage forms of the present invention represent from about 1 to about 60% by weight of the solid dosage form and include microcrystalline cellulose (MCC). Preferably, the solid dosage forms contain from about 2 to about 25 and most preferably about 5 to about 20% by weight direct compression vehicle.

Microcrystalline cellulose is a well-known tablet diluent and disintegrant. Its chief advantage over other excipients is that it can be directly compressed into self-binding tablets which disintegrate rapidly when placed into water. This widely-used ingredient is prepared by partially depolymerizing cellulose obtained as a pulp from fibrous plant material with dilute mineral acid solutions. Following hydrolysis, the hydrocellulose thereby obtained is purified via filtration and the aqueous slurry is spray dried to form dry, white odorless, tasteless crystalline powder of porous particles of a broad size distribution. Another method of preparing microcrystalline cellulose is disclosed in U.S. Pat. No. 3,141,875. This reference discloses subjecting cellulose to the hydrolytic action of hydrochloric acid at boiling temperatures so that amorphous cellulosic material can be removed and aggregates of crystalline cellulose are formed. The aggregates are collected by filtration, washed with water and aqueous ammonia and disintegrated into small fragments, often called cellulose crystallites by vigorous mechanical means such as a blender. Microcrystalline cellulose is commercially available in several grades which range in average particle size from 20 to 200 microns.

Microcrystalline cellulose is water-insoluble, but the material has the ability to draw fluid into a tablet by capillary action. The tablets then swell on contact and the microcrystalline cellulose thus acts as a disintegrating agent. The material has sufficient self-lubricating qualities so as to allow a lower level of lubricant as compared to other excipients.

Typically, microcrystalline cellulose bulk powder has an apparent density of about 0.28 g/cm$^3$ and a tap density of about 0.43 g/cm$^3$. *Handbook of Pharmaceutical Excipients*, pages 53–55.

When utilized in pharmaceutical applications, microcrystalline cellulose is typically used as a tablet binder/diluent in wet granulation and direct compression formulations in amounts of 5–30% of the formulation, or more. However, it is known to use more or less microcrystalline cellulose in pharmaceutical products, depending upon the requirements of the formulation. In spite of it being known to include MCC in direct compression formulations, mere twin shell blending of APAP and MCC has not provided a mixture which could be direct compressed into an acceptable solid dosage form.

In one preferred embodiment of the invention, the direct compression vehicle includes a microcrystalline cellulose which has been coprocessed with from about 0.1 to about 20% silicon dioxide. This coprocessed, direct compression vehicle is an agglomerate of microcrystalline cellulose and: silicon dioxide in which the micro-crystalline cellulose and silicon dioxide are in intimate association with each other such as that described in commonly-assigned U.S. patent application Ser. No. 08/370,576, the disclosure of which is incorporated by reference herein. Magnifications of these coprocessed particles indicate that the silicon dioxide is integrated with, or partially coats, the surfaces of the microcrystalline cellulose particles.

The exact relationship of the two ingredients in the excipient after coprocessing is not presently understood; however, for purposes of description, the coprocessed particles are described herein as including an agglomerate of microcrystalline cellulose and silicon dioxide in intimate association with each other. By "intimate association", it is meant that the silicon dioxide has in some manner been integrated with the microcrystalline cellulose particles, e.g., via a partial coating of the microcrystalline particles, as opposed to a chemical interaction of the two ingredients. The term "intimate association" is therefore deemed for purposes of the present description as being synonymous with "integrated" or "united". The coprocessed particles are not necessarily uniform or homogeneous. Rather, under magnification, e.g., scanning electron microscope at 500×, the silicon dioxide at the preferred percent inclusion appears to be an "edge-coating".

The compressed excipient has a bulk (loose) density ranging from about 0.2 g/ml to about 0.6 g/ml, and most preferably from about 0.35 g/ml to about 0.55 g/ml. The coprocessed excipient has a tapped density ranging from about 0.25 g/ml to about 0.65 g/ml, and most preferably from about 0.35 g/ml to about 0.55 g/ml. The pH of the particles is most preferably about neutral, although granulates having a pH of from about 3.0 to about 8.5 are possible. The moisture content of the excipient particles will broadly range from about 0.5% to about 15%, preferably from about 1.5% to about 7%, and most preferably from about 3.0% to about 5% by weight.

The coprocessed excipient can be used alone or in combination with "off-the-shelf" MCC in any desired proportion to form the direct compression vehicle included in the novel dosage forms.

The silicon dioxide coprocessed with microcrystalline in this aspect of the invention preferably has an average primary particle size of from about 1 nm to 1,000 μm. More preferably, however, the silicon dioxide has an average primary size of from about 5 nm to 40 μm.

The silicon dioxide coprocessed with the MCC is preferably derived from colloidal silicon dioxide and, preferably comprises from about 0.5 to 10% by weight of the coprocessed material based on the weight of the microcrystalline cellulose and, more preferably, comprises from about 1.25 to about 5% by weight of the agglomerate based on the weight of the microcrystalline cellulose.

Lubricants

The solid dosage forms of the present invention also include a sufficient amount of a lubricant. In preferred aspects of the invention, the lubricant selected is sodium stearyl fumarate. Alternatives, however, include magnesium stearate, hydrogenated vegetable oil, LUBRITAB® (Edward Mendell Co., Inc.), stearic acid, PEG, and other lubricants known to those of ordinary skill in the art. In this regard, the lubricant will be present in amounts ranging from about 0.01 to about 4.0% by weight of the dosage form. Amounts of from about 0.1 to about 1.0% by weight are preferred and amounts of from about 0.2 to about 0.45% are most preferred.

In accordance with the present, invention, the lubricant is combined with the homogeneous mixture containing the APAP and direct compression vehicle. It has been surprisingly found that high shear blending of the lubricant with the homogeneous granulate does not adversely affect the tablet hardness of direct compressed dosage forms. While Applicants are not bound by theory, it is proposed that the high shear mixing conditions convey physical properties on the lubricant-containing granulate which are completely contrary to what was expected and which are desirable for direct compression of the granulation.

Additional Ingredients

A. Silicon Dioxide

In certain preferred aspects of the invention, the direct compressed pharmaceutical dosage forms include silicon dioxide in an amount which is separate from and in addition to the silicon dioxide included with the coprocessed MCC (if used). In this regard, the silicon dioxide is preferably colloidal silicon dioxide and is present in an amount of from about 0.1 to about 5% by weight of the dosage form. Preferably, however, the silicon dioxide is present in an amount of from about 0.15 to about 0.9% by weight and most preferably in an amount of from about 0.4 to about 0.75% by weight of the dosage form.

Silicon dioxide is obtained by insolubilizing dissolved silica in sodium silicate solution. When obtained by the addition of sodium silicate to a mineral acid, the product is termed silica gel. When obtained by the de-stabilization of a solution of sodium silicate in such a manner as to yield very fine particles, the product is termed precipitated silica. Silicon dioxide is insoluble in water. Silicon dioxide, and in particular colloidal silicon dioxide, is mainly used as a glidant and anti-adherent in tableting processes and encapsulation to promote the flowability of the granulation. *Handbook of Pharmaceutical Excipients*, ©1986 American Pharmaceutical Association, page 255. This is due in part to the fact that increasing the amount of silicon dioxide in the mixture to be tableted causes the mixture to flow too well, causing a phenomena known to those skilled in the tableting art as "flooding". If the mixture flows too well, a varying tablet weight with uneven content uniformity can result.

Those skilled in the art will appreciate that the name and/or method of preparation of the silicon dioxide utilized in the present invention is not determinative of the usefulness of the product. Rather, it has been surprisingly discovered that high shear mixing of $SiO_2$ with other formulation ingredients unexpectedly enhances tablet hardness in direct compression dosage forms.

The present invention encompasses all forms of silicon dioxide having an average primary particle size from about 1 nm to about 100 μm, and/or a surface area from about 10 $m^2/g$ to about 500 $m^2/g$.

The silicon dioxide utilized in the invention is of the very fine particle size variety. In the most preferred embodiments of the invention, the silicon dioxide utilized is a colloidal silicon dioxide. Colloidal silicon dioxide is a submicron fumed silica prepared by the vapor-phase hydrolysis (e.g., at 1110° C.) of a silicon compound, such as silicon tetrachloride. The product itself is a submicron, fluffy, light, loose, bluish-white, odorless and tasteless amorphous powder which is commercially available from a number of sources, including Cabot Corporation (under the tradename Cab-O-Sil); Degussa, Inc. (under the tradename Aerosil); E.I. DuPont & Co.; and W.R. Grace & Co. Colloidal silicon dioxide is also known as colloidal silica, fumed silica, light anhydrous silicic acid, silicic anhydride, and silicon dioxide fumed, among others. A variety of commercial grades of colloidal silicon dioxide are produced by varying the manufacturing process. These modifications do not affect the silica content, specific gravity, refractive index, color or amorphous form. However, these modifications are known to change the particle size, surface areas, and bulk densities of the colloidal silicon dioxide products.

The surface area of the preferred class of silicon dioxides utilized in the invention ranges from about 50 $m^2/gm$ to about 500 $m^2/gm$. The average primary particle diameter of the preferred class of silicon dioxides utilized in the invention ranges from about 5 nm to about 50 nm. However, in commercial colloidal silicon dioxide products, these particles are agglomerated or aggregated to varying extents. The bulk density of the preferred class of silicon dioxides utilized in the invention ranges from about 20 g/l to about 100 g/l.

Commercially available colloidal silicon dioxide products have, for example, a BET surface area ranging from about 50±15 $m^2/gm$ (Aerosil OX50) to about 400±20 (Cab-O-Sil S-17) or 390±40 $m^2/gm$ (Cab-O-Sil EH-5). Commercially available particle sizes range from a nominal particle diameter of 7 nm (e.g., Cab-O-Sil S-17 or Cab-O-Sil EH-5) to an average primary particle size of 40 nm (Aerosil OX50). The density of these products range from 72.0±8 g/l (Cabo-Sil S-17) to 36.8 g/l (e.g., Cab-O-Sil M-5). The pH of the these products at 4% aqueous dispersion ranges from pH 3.5–4.5. These commercially available products are described for exemplification purposes of acceptable properties of the preferred class of silicon dioxides only, and this description is not meant to limit the scope of the invention in any manner whatsoever.

In those aspects of the invention where the silicon dioxide is a part of the pharmaceutical dosage form, it is preferred that the silicon dioxide be combined with the acetaminophen, direct compression vehicle and lubricant under the same high shear conditions used to create the homogenous mixture of the solid dosage form ingredients. Alternatively, the silicon dioxide can be high shear blended with the acetaminophen and direct compression vehicle before the lubricant is combined therewith.

B. Disintegrant

A disintegrant may also be included with the other solid dosage form ingredients and subjected to the high shear mixing and, therefore, become part of the homogenous mixture. In one preferred aspect of the invention, the disintegrant is sodium starch glycolate and will be present in amounts ranging from 0.01 to about 4.0% by weight of the dosage form, preferably from about 0.1 to about 2.0% and most preferably in amounts ranging from about 1.00 to about 1.50% by weight of the dosage form one particularly useful disintegrant is available under the trademark Explotab™ available from Edward Mendell Co., Inc. Alternative disintegrants include, for example, carboxymethylcellulose, cross-linked polyvinyl pyrrolidones in amounts similar to that set forth above or starches, in amounts of from around 4 to about 5%.

C. Ancillary Pharmaceutical Ingredients

The solid dosage form can also include an inert pharmaceutical filler such as a monosaccharide, a disaccharide, a polyhydric alcohol, inorganic phosphates, sulfates or carbonates, and/or mixtures thereof. Examples of suitable inert pharmaceutical fillers include sucrose, dextrose, lactose, xylitol, fructose, sorbitol, calcium phosphate, calcium sulfate, calcium carbonate, mixtures thereof, and the like. The amount of inert filler, if included, will be an amount which does not detract from the enhanced tablet hardness achieved by the novel process described herein. In this regard, the amount will be less than 10% by weight of the tablet.

Shear Mixing Conditions

The present invention includes transforming acetaminophen, a direct compression vehicle and optionally, a pharmaceutically-acceptable lubricant into a homogenous granulate under shear conditions which do not degrade the ingredients. For purposes of the present invention, the shear conditions under which the ingredients are combined can generally be described as a set of conditions including a combination of temperature and mechanical forces which permit the formation of the homogenous granulate but do not break down the materials undergoing the processing. For purposes of the present invention, the conditions are described as high shear to distinguish them from the standard blending achieved by twin shell mixing or tumbling. Suitable apparatus for carrying out the high shear mixing contemplated herein can include high speed mixers having an impeller or mixing blade rotating about a central shaft close to the bottom of the mixing bowl and a chopper or series of choppers which consist of fast rotating arms or knives which are inserted into the mixing bowl. This combination of mixing and chopping confers a mechanical influence or force on the APAP and MCC which transforms them into a homogeneous mixture which can be direct compressed even if the APAP constitutes the majority of the granulate on a weight basis. One high shear granulator having an impeller and high shear chopper is available from Baker-Perkins. While such apparatus is usually used to prepare wet granulations, it has been found that when the apparatus is operating under dry mixing conditions, it is capable of transforming the solid dosage form ingredients under shear conditions into the homogenous mixture. In this particular apparatus, the operation of the impeller in combination with the chopper creates the shear mixing environment. One useful set of parameters with this apparatus for rendering the necessary high shear conditions includes operating the impeller at about 100 to 300 rpm and the chopper from about 200 to about 1,200 rpm. It will be understood, however, that the speeds of the impeller and chopper can extend beyond the ranges provided with regard to the illustrative device and that optimum operating conditions for alternative shear mixing apparatus will be apparent to those of ordinary skill without undue experimentation. The simultaneous action of the impeller and chopper have been found to uniquely transform the solid dosage form ingredients into a mixture which can be directly compressed into solid pharmaceutical dosage forms having sufficient hardness and size characteristics suitable for oral delivery of even high load-containing tablets. It is to be understood, however, that the Baker-Perkins apparatus described above is merely illustrative of the type of apparatus useful in transforming the dosage form ingredients. Those of ordinary skill in the art will realize that other high shear mixing devices can be used, such as a Patterson-Kelly twin shell mixing apparatus equipped with an intensifier bar to facilitate mixing, chopping, shear forces and counter rotating of the ingredients. The Gral high shear mixer available from Machines Collette., Inc. Totowa, N.J. operating under dry conditions can also be used.

In another aspect of the invention, the shear mixing conditions used to transform the APAP and direct compression vehicle are expressed as a measurement of the vigorousness of the mechanical processing. One such measurement is the relative swept volume, a ratio of the volume through which the impeller travels every second to the volume of the bowl. The size of the swept volume is calculated by dividing the area of each impeller blade into vertical segments and on the impeller velocity, calculating the volume the impeller blades travel through per second.

In preferred aspects of the invention, the solid dosage forms of the present invention are prepared from a homogenous granulate prepared as a result of a two step, high shear mixing technique. In the first step, the acetaminophen, direct compression vehicle, and, optionally, disintegrant and/or silicon dioxide, are combined under high shear conditions to form a first high shear mixture which preferably contains the ingredients in a homogenous distribution. The second step includes combining the first high shear mixture with the lubricant under high shear conditions to form the final homogenous granulate. In preferred aspects of this embodiment, the shear force used to combine the lubricant with the first high shear mixture is less than that used to combine the ingredients of the first high shear mixture.

Direct Compression of APAP Granulate

The present invention also includes methods of preparing solid pharmaceutical dosage forms containing APAP via direct compression. As pointed out above, direct compression techniques include compressing tablet ingredients directly without modifying the physical nature of any of the ingredients. In this regard, therefore, the methods include:

a) combining from about 40 to about 95% by weight acetaminophen and from about 1 to about 60% by weight of a direct compression vehicle comprising microcrystalline cellose under shear conditions which are sufficient to transform the acetaminophen and direct compression vehicle into a first homogenous granulate;

b) combining the first homogenous granulate with from about 0.01 to about 4.0% of a pharmaceutically-acceptable lubricant; and c) compressing the homogenous granulate containing the lubricant into a solid pharmaceutical dosage form.

It is to be understood that the combining steps described above are preferably carried out in the high shear mixing apparatus described above.

In preferred embodiments of the present invention, the APAP is in granular form having a particle size of from about 250 to about 500 microns and the direct compression vehicle includes co-processed MCC.

An alternative method in accordance with the present invention includes combining from about 0.1 to about 5% by weight silicon dioxide with the APAP and direct compression vehicle and subjecting this mixture to the shear mixing conditions described herein. A disintegrant can also be included in this high shear mixture designated herein as a first homogeneous granulate. The lubricant can be combined with the first homogeneous granulate either by additional high shear mixing or by other blending techniques such as twin shell blending. It is preferred, however, that the lubricant be combined with the first homogeneous granulate by additional high shear mixing. In this regard, it is preferred that the high shear blending used to incorporate the lubricant be carried out under shear conditions which are less than those used to prepare the first homogeneous granulate. Thus, the lubricant will preferably be added under shear conditions which include one or more reductions in the mixing parameters i.e. lower mixing or chopping rpm's and/or shorter mixing times.

The complete homogeneous high shear mixture, in an amount sufficient to make a uniform batch of tablets, is then subjected to tableting in a conventional production scale direct compression tableting machine at normal compression pressures for that machine, e.g., about 1500–10,000 lbs/sq in. The mixture should not be compressed to such a degree that there is subsequent difficulty in its hydration when exposed to gastric fluid.

As pointed out above, the solid dosage forms of the present invention will contain from 10 to about 1000 milligrams of APAP. The average tablet size for the direct compressed tablets will therefore range from about 50 mg to 2000 mg. Other formulations prepared in accordance with the present invention may be suitably shaped for other uses or locations, such as other body cavities, e.g., periodontal pockets, surgical wounds, vaginally. It is contemplated that for certain uses, e.g., antacid tablets, vaginal tablets and possibly implants, that the tablet will be larger.

One particularly preferred solid dosage form of the present invention contains at least about 75% by weight APAP and has an average tablet hardness of about 6.5 kP when the homogeneous granulate is direct compressed at a compression force of about 25 kN.

In certain embodiments of the invention, the tablet is coated with a sufficient amount of a hydrophobic polymer to render the formulation capable of providing, a release of the medicament such that a 12 or 24 hour formulation is obtained. The hydrophobic polymer can be selected from materials well known to those of ordinary skill in the art such as acrylic acid derivatives. In other embodiments of the present invention, the tablet coating may comprise an enteric coating material in addition to or instead or the hydrophobic polymer coating. Examples of suitable enteric polymers include cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. An example of a suitable commercially available enteric material is available under the trade name Eudragit™ L 100–555.

In further embodiments, the dosage form may be coated with a hydrophilic coating in addition to or instead of the above-mentioned coatings. An example of a suitable material which may be used for such a hydrophilic coating is hydroxypropylmethylcellulose (e.g., Opadry®, commercially available from Colorcon, West Point, Pa.).

The coatings may be applied in any pharmaceutically acceptable manner known to those skilled in the art. For example, in one embodiment, the coating is applied via a fluidized bed or in a coating pan. For example, the coated tablets may be dried, e.g., at about 60–70° C. for about 3–4 hours in a coating pan. The solvent for the hydrophobic polymer or enteric coating may be organic, aqueous, or a mixture of an organic and an aqueous solvent. The organic solvents may be, e.g., isopropyl alcohol, ethanol, and the like, with or without water.

The coatings which may be optionally applied to the compressed solid dosage form of the invention may comprise from about 0.5% to about 30% by weight of the final solid dosage form.

In additional embodiments of the present invention, a support platform is applied to the tablets manufactured in accordance with the present invention. Suitable support platforms are well known to those skilled in the art. An example of suitable support platforms is set forth, e.g., in U.S. Pat. No. 4,839,177, hereby incorporated by reference. In that patent, the support platform partially coats the tablet, and consists of a polymeric material insoluble in aqueous liquids. The support platform may, for example, be designed to maintain its impermeability characteristics during the transfer of the therapeutically active medicament. The support platform may be applied to the tablets, e.g., via compression coating onto part of the tablet surface, by spray coating the polymeric materials comprising the support platform onto all or part of the tablet surface, or by immersing the tablets in a solution of the polymeric materials.

The support platform may have a thickness of, e.g., about 2 mm if applied by compression, and about 10 μm if applied via spray-coating or immersion-coating. Generally, in embodiments of the invention wherein a hydrophobic polymer or enteric coating is applied to the tablets, the tablets are coated to a weight gain from about 1% to about 20%, and in certain embodiments preferably from about 5% to about 10%.

Materials useful in the hydrophobic coatings and support platforms of the present invention include derivatives of acrylic acid (such as esters of acrylic acid, methacrylic acid, and copolymers thereof) celluloses and derivatives thereof (such as ethylcellulose), polyvinylalcohols, and the like.

In certain embodiments of the present invention, the tablet core includes an additional dose of a medicament, i.e. APAP, included in either the hydrophobic or enteric coating, or in an additional overcoating coated on the outer surface of the tablet core (without the hydrophobic or enteric coating) or as a second coating layer coated on the surface of the base coating comprising the hydrophobic or enteric coating material. This may be desired when, for example, a loading dose of APAP is needed to provide therapeutically effective blood levels when the formulation is first exposed to gastric fluid. The loading dose of medicament included in the coating layer may be, e.g., from about 10% to about 40% of the total amount of medicament included in the formulation.

The solid formulations of the invention may also include other locally active agents, such as flavorants and sweeteners. Generally any flavoring or food additive such as those described in *Chemicals Used in Food Processing*, pub 1274 by the National Academy of Sciences, pages 63–258 may be used. Generally, the final product may include from about 0.1% to about 5% by weight flavorant.

The tablets of the present invention may also contain effective amounts of coloring agents, (e.g., titanium dioxide, F.D. & C. and D. & C. dyes; see the Kirk-Othmer Encyclopedia of Chemical Technology, Vol. 5, pp. 857–884, hereby incorporated by reference), stabilizers, binders, odor controlling agents, and preservatives.

Alternatively, the novel homogenous high shear granulate can be utilized in other applications wherein it is not compressed. For example, the granulate can be filled into capsules. The granulate can further be molded into shapes other than those typically associated with tablets. For example, the granulate together with acetaminophen can be molded to "fit" into a particular area in an environment of use (e.g., an implant). All such uses would be contemplated by those skilled in the art and are deemed to be encompassed within the scope of the appended claims.

A still further embodiment of the present invention is directed to a method of effecting analgesia in mammals. This method includes administering a dosage form described herein containing an effective amount of APAP to a mammal in need of such treatment. In preferred aspects of this embodiment, the dosage forms contain from about 10 to about 1000 milligrams of APAP and more preferably, from about 120 to about 750 milligrams of APAP. For purposes of the present invention, the term "effective amount" shall be understood to include a generally accepted amount of APAP for purposes of effecting analgesia for mild to moderate pain. The method of treatment can also include administering the effective amount as a single dose or as multiple doses administered every four to six hours as needed.

A still further aspect of the invention includes homogeneous high-shear granulates which are useful as pharmaceutical intermediates. The granulates include:

a) from about 94 to about 99.99% by weight of a direct compression vehicle comprising microcrystalline cellulose; and b) from about 0.01 to about 6.0% by weight of a pharmaceutically-acceptable lubricant.

The direct compression vehicle and pharmaceutically-acceptable lubricant are combined under shear conditions which are sufficient to transform the direct compression vehicle and pharmaceutically-acceptable lubricant into a homogenous granulate without degradation. The intermediates are thus suitable for admixture with one or more active ingredients such as by additional high shear mixing and thereafter direct compression into a solid pharmaceutical dosage form.

The shear conditions under which the intermediate ingredients are combined are similar to that used for the APAP formulations described above. In addition, all other direct compression ingredients, such as disintegrants, etc., can also be included in the intermediate product as well.

DETAILED DESCRIPTION OF THE PREFERRED EMBODIMENTS

The following examples illustrate various aspects of the present invention. They are not to be construed to limit the claims in any manner whatsoever.

The examples set forth the preparation of pharmaceutical compositions containing a high load of the active ingredient acetaminophen (APAP) in combination with microcrystalline cellulose based excipients. Tablets were prepared using each of the compositions and each of tablet preparations was tested for tensile strength.

EXAMPLES 1–2

Preparation of Coprocessed MCC-$SiO_2$ Compositions and Granulations Thereof

Example 1

MCC-$SiO_2$ Product-5% w/w $SiO_2$

In this example, about 6.2 kilograms of microcrystalline cellulose (MCC), (Mendell Co., Inc. Patterson, N.Y.) in the form of a wet cake was combined with 5.2 kilograms of water in a mix tank to form a slurry containing about 15% solids. The pH was adjusted to about neutral with about 3 ml of ammonium hydroxide. The slurry was allowed to mix for about 15 minutes before being combined with 5% w/w colloidal silicon dioxide (CSD), 200 $m^2$/g (CaboSil, PTG grade, available from Cabot Corp., Tuscola, Ill.) After allowing the materials to become intimately combined, the slurry was spray dried using a Niro Production Minor (Niro, Columbia, Md.), inlet temperature-215° C., outlet temperature-125° C., atomizer wheel speed 22,300 rpm, to provide MCC-$SiO_2$ having an average particle size of 40–60 microns.

Example 2

MCC-SiO$_2$ Product-2% w/w SiO$_2$

In this example, the process of Example 1 was repeated except that 2% w/w colloidal silicon dioxide was used to form the product.

EXAMPLES 3–11

In these examples, batches of compressed tablets containing granular acetaminophen (APAP) in high load (80% wt.) were prepared using the techniques described herein and compared to a high load (80% by weight) APAP formulation described above wherein all ingredients were V-blended before being compressed into tablets.

In each case, the tablets were prepared using a Korsch tablet press having a punch size of ⅜" and an aim weight of about 245 mg±5 mg. Each of the foregoing granulations was included in five separate tableting runs using compression forces of 6, 12, 18, 24 and 30 kN, respectively. Ten tablets from each run were weighed, measured for diameter and tested for thickness and hardness on the Erweka TBH 30 tablet hardness tester to determine tensile strength of the final product. The results of the analyses are graphically illustrated in FIGS. 1–2 as a comparison of tensile strength versus compression force.

The batch formula for the comparative control tablets is set forth below:

| COMPARATIVE BATCH | | |
|---|---|---|
| INGREDIENT | BATCH % | GRAMS PER BATCH |
| Microcrystalline cellulose (MCC) | 17.80% | 44.50 |
| APAP | 80.00% | 200.00 |
| Sodium starch glycolate (SSG) | 2.00% | 5.00 |
| Mg. Stearate | 0.20% | 0.50 |
| TOTAL | 100.00% | 250.00 |

The MCC, APAP and SSG were added to a two quart V-blender and mixed for 15 minutes. Thereafter, the Mg stearate was added to the blender and mixing was continued for an additional 5 minutes. All mixing of the ingredients was carried out in a room having a relative humidity of about 10%. The mixture was then removed from the blender and tableted in the same manner as that used to prepare the tablets of the invention.

Example 3

In this example, compressed tablets containing APAP were prepared according to the batch formula set forth below. The microcrystalline cellulose used was the MCC coprocessed with 5.0% SiO$_2$ as described in Example 1.

| INGREDIENT | BATCH % | GRAMS PER BATCH |
|---|---|---|
| MCC coprocessed w/5% CSD | 17.60% | 88.00 |
| APAP | 80.00% | 400.00 |
| Colloidal silicon dioxide (CSD) | 0.50% | 2.50 |
| Sodium starch glycolate (SSG) | 1.50% | 7.50 |
| Sodium stearyl fumarate (SSF) | 0.40% | 2.00 |
| TOTAL | 100.00% | 500.00 |

The tablets were prepared according to the following procedure:

The coprocessed MCC was added to a Baker-Perkins 10 L high shear granulator along with the APAP, CSD and SSG. The CSD added was in addition to that included in the coprocessed MCC. The ingredients are mixed under dry, high shear conditions for 3 minutes with the impeller set at 200 rpm and the chopper at 1,000 rpm. Thereafter, the sodium stearyl fumarate, PRUV™, Edward Mendell Co., Inc., was added to the high shear granulator and mixing was continued for an additional 25 seconds with the impeller at 200 rpm and the chopper at 500 rpm. At the conclusion of this mixing step, the dry granulate was removed and directly compressed into tablets using the aforementioned Korsch PH-100 tablet press and compression forces.

Example 4

In this example, the procedure of Example 3 was repeated except that the MCC used was "off-the-shelf" MCC (EMCOCEL®, Edward Mendell Co., Inc.) rather than the silicon dioxide coprocessed material of Example 1. The tablets were prepared using the following batch formula:

| INGREDIENT | BATCH % | GRAMS PER BATCH |
|---|---|---|
| MCC (off-the-shelf) | 17.60% | 88.00 |
| APAP | 80.00% | 400.00 |
| Colloidal silicon dioxide (CSD) | 0.50% | 2.50 |
| Sodium starch glycolate (SSG) | 1.50% | 7.50 |
| Sodium stearyl fumarate (SSF) | 0.40% | 2.00 |
| TOTAL | 100.00% | 500.00 |

Example 5

In this example, the procedure of Example 3 was repeated except that additional CSD was not included in the high shear mixing of the ingredients. The batch formula set forth below was used.

| INGREDIENT | BATCH % | GRAMS PER BATCH |
|---|---|---|
| MCC coprocessed w/5% CSD | 18.10% | 90.50 |
| APAP | 80.00% | 400.00 |
| Sodium starch glycolate (SSG) | 1.50% | 7.50 |
| Sodium stearyl fumarate (SSF) | 0.40% | 2.00 |
| TOTAL | 100.00% | 500.00 |

Example 6

In this example an additional control granulation was prepared by V-blending mixing off-the-shelf MCC with the other ingredients in a controlled environment having a relative humidity of about 40%. The granulation also did not include any added silicon dioxide. The formulation was prepared according to the following batch formula:

| INGREDIENT | BATCH % | GRAMS PER BATCH |
|---|---|---|
| MCC | 18.10% | 90.50 |
| APAP | 80.00% | 400.00 |
| Sodium starch glycolate (SSC) | 1.50% | 7.50 |
| Sodium stearyl fumarate (SSF) | 0.40% | 2.00 |
| TOTAL | 100.00% | 500.00 |

Example 7

In this example, the procedure of Example 3 was followed. In this batch, however, the MCC used was the coprocessed product of Example 2 which contained 2.0% SiO$_2$. The batch also did not include a separate amount of added CSD in the high shear mixture.

| INGREDIENT | BATCH % | GRAMS PER BATCH |
|---|---|---|
| MCC coprocessed w/2% CSD | 18.10% | 90.50 |
| APAP | 80.00% | 400.50 |
| Sodium starch glycolate (SSG) | 1.50% | 7.55 |
| Sodium stearyl fumarate (SSF) | 0.40% | 2.00 |
| TOTAL | 100.00% | 500.00 |

Example 8

In this example, the directly compressed tablets containing APAP were prepared using the procedure of Example 3 except that the MCC used was the coprocessed microcrystalline cellulose of Example 2. The batch formula set forth below was used.

| INGREDIENT | BATCH % | GRAMS PER BATCH |
|---|---|---|
| MCC coprocessed w/2% CSD | 17.60% | 88.00 |
| APAP | 80.00% | 400.00 |
| Colloidal silicon dioxide (CSD) | 0.50% | 2.50 |
| Sodium starch glycolate (SSG) | 1.50% | 7.50 |
| Sodium stearyl fumarate (SSF) | 0.40% | 2.00 |
| TOTAL | 100.00% | 500.00 |

Discussion

Referring now to FIG. 1, the results of the tensile strength tests for the directly-compressed high load tablets are discussed. Each of the high load-containing APAP tablets made in accordance with the present invention had a desirable tablet hardness profile when compared to that of the V-blended comparative example.

It can also be seen that mere dry blending of the ingredients prior to direct compression did not provide acceptable tensile strength. Even in the case of Example 6, where humidity was increased to about 40%, the results failed to match that obtained by the high shear mixing of the present invention. Furthermore, the advantages of high shear blending the APAP and MCC-based compression vehicle is especially apparent at higher compression forces. The results also point up the fact that those high load tablets prepared with MCC coprocessed with SiO$_2$, i.e. Examples 3 and 8 as well as those containing a separately added amount of SiO$_2$, i.e. Example 4, have a particularly desirable tablet hardness profile.

In general, the results obtained for the inventive compositions were completely unexpected since those of ordinary skill in the art are well aware of the problems associated with combining tablet lubricants such as sodium stearyl fumarate with the other tablet ingredients under high shear conditions. Contrary to what was expected, the directly compressed high load tablets had higher rather than lower tensile strength. Further, the overcoating of the granules with the lubricant which was expected and which would have significantly reduced the tablet hardness was not observed. In addition, it was also unexpected that granular forms of APAP would provide the necessary physical characteristics to a formulation to allow formation of direct compressed high load tablets having acceptable levels of hardness. Thus, it can be seen that the high shear mixing of MCC-based excipients as described herein directly addresses a shortcoming of the prior art techniques.

Example 9

In this example, the tablets were prepared according to the following batch formula:

| INGREDIENT | BATCH % | GRAMS PER BATCH |
|---|---|---|
| MCC (coprocessed w/2% CSD) | 17.60% | 88.00 |
| APAP | 80.00% | 400.0 |
| Colloidal silicon dioxide (CSD) | 0.50% | 2.50 |
| Sodium starch glycolate (SSG) | 1.50% | 7.50 |
| Sodium stearyl fumarate (SSF) | 0.40% | 2.00 |
| TOTAL | 100.00% | 500.00 |

In this example, the initial high shear mixing of the MCC, APAP, CSD, and SSG was carried out in the same manner as described above with regard to Example 4 (i.e., using the high shear blender for 3 minutes at 200 rpm for impeller and 1,000 rpm for chopper). However, after this first high shear mixing step, all ingredients were removed and transferred to a 2 quart V-blender. No further high shear mixing was undertaken. Instead, the sodium stearyl fumarate was added to the mixture and V-blender mixing was carried out for 5 minutes. The tablets were then made following the procedures described above.

Example 10

The procedure of Example 11 was repeated except that an equal amount of magnesium stearate was substituted for the sodium stearyl fumarate used in Example 11 for the V-blending step prior to the direct compression of the tablets.

| INGREDIENT | BATCH % | GRAMS PER BATCH |
|---|---|---|
| MCC (coprocessed w/2% CSD) | 17.60% | 88.00 |
| APAP | 80.00% | 400.0 |
| Colloidal silicon dioxide (CSD) | 0.50% | 2.50 |

-continued

| INGREDIENT | BATCH % | GRAMS PER BATCH |
|---|---|---|
| Sodium starch glycolate (SSG) | 1.50% | 7.50 |
| Magnesium stearate | 0.40% | 2.00 |
| TOTAL | 100.00% | 500.00 |

Example 11

In this example, the two step high shear blending procedure of Example 4 was repeated except that magnesium stearate was substituted for the originally described sodium stearyl fumarate. As was the case in Example 4, high shear mixing was used for both performing both the initial and final blends.

| INGREDIENT | BATCH % | GRAMS PER BATCH |
|---|---|---|
| MCC (off-the-shelf) | 17.60% | 88.00 |
| APAP | 80.00% | 400.00 |
| CSD | 0.50% | 2.50 |
| SSG | 1.50% | 7.50 |
| Magnesium stearate | 0.40% | 2.00 |
| TOTAL | 100.00% | 500.00 |

Discussion

Figure 2:
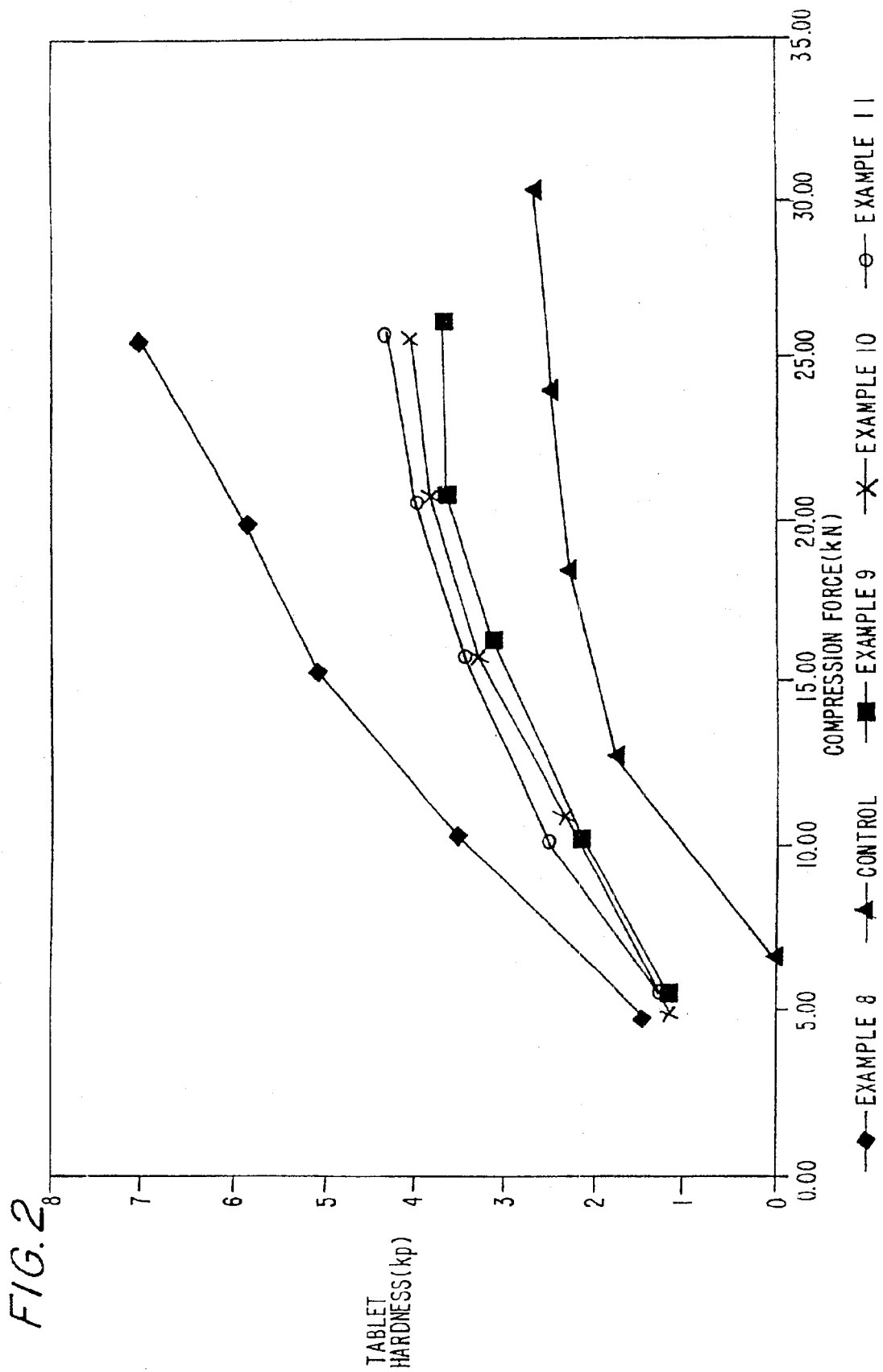
FIG. 2 graphically illustrates a comparison of the tensile strength of tablets prepared in accordance with Examples 8 and 9–11 and that obtained for a control high load APAP formulation.

FIG. 2 graphically provides the results for the comparison of the two step high shear mixed, direct compressed tablets of Example 8 with the high shear, then low shear mixed formulations of Examples 9 and 10 and the V-blended control formulation. The graph also provides the results for the two step high shear formulation of Example 11, which included magnesium stearate instead of sodium stearyl fumarate in the second high shear mixing step.

In each case, it can be seen that improvements in tablet hardness can be realized even if the lubricant is combined under low shear conditions. In all cases, the tablets prepared from granulations which were prepared using at least one high shear mixing step out-performed the completely V-blended control.

EXAMPLE 12

Figure 3:
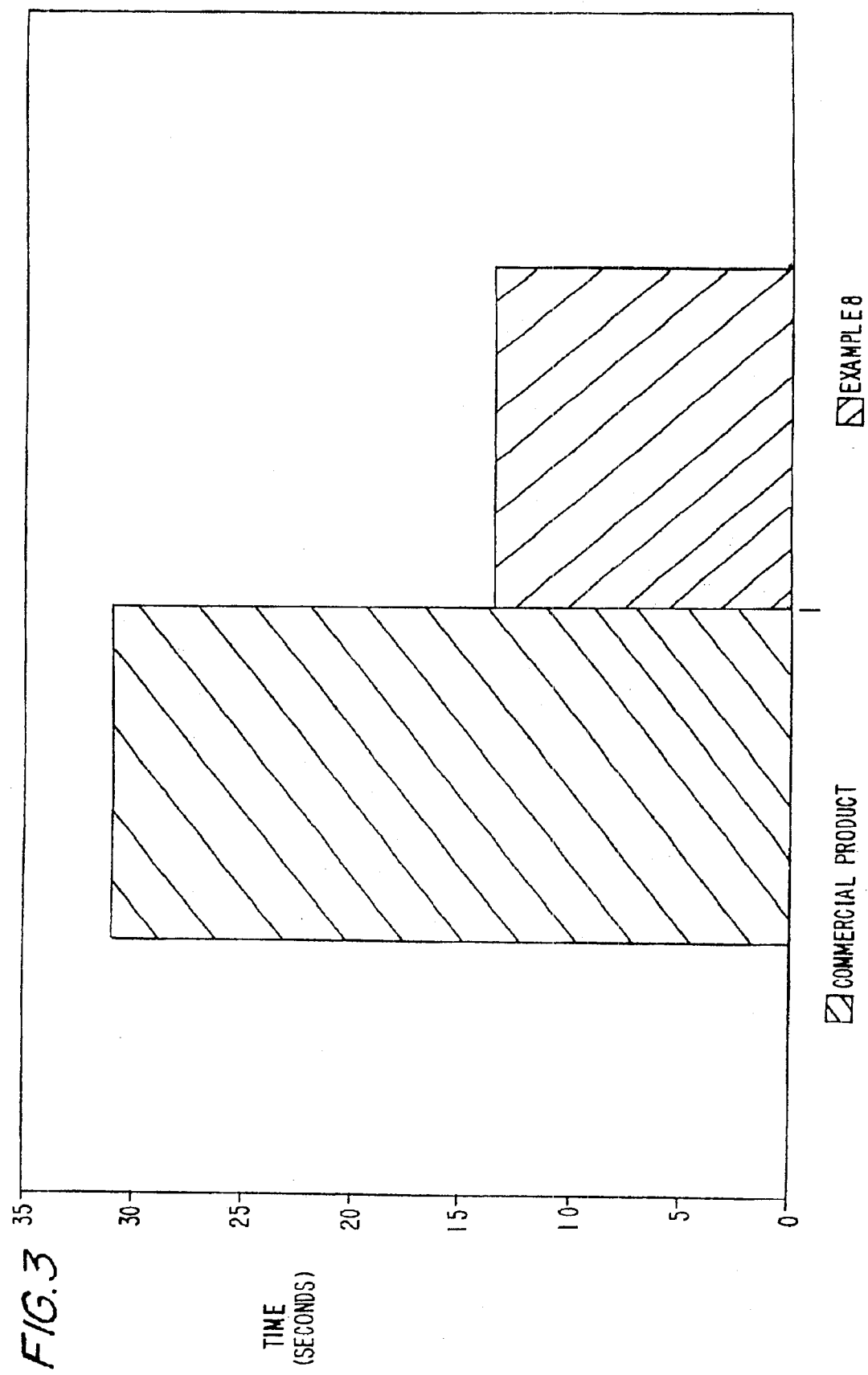
FIG. 3 is a graphic illustration of the differences in the disintegration time for a batch of tablets prepared in accordance with the present invention and commercially available APAP tablets.

In this example, the average disintegration time for tablets prepared in accordance with Example 8 was determined and compared to that of commercially available APAP tablets sold under the Tylenol® brand. The test was carried out according to the U.S.P. guidelines using a Van-Kel disintegration apparatus. In particular, six tablets prepared according to the procedure of Example 8 as well as six Tylenol tablets were individually evaluated in the apparatus to determine disintegration time in deionized water at 37° C. without using the basket disk of the apparatus. The average disintegration time for the six tablets in each group was then calculated and illustrated as a graph which is set forth as FIG. 3.

As can be seen from the graph, the tablets prepared in accordance with the present invention had an average disintegration time of less than half of that required for the commercially sold formulation. This rapid disintegration feature illustrates an additional advantage of the formulations of the present invention.

While there have been described what are presently believed to be the preferred embodiments of the invention, those skilled in the art will realize that changes and modifications may be made thereto without departing from the spirit of the invention. It is intended to claim all such changes and modifications that fall within the true scope of the invention.

What is claimed is:

1. A direct compressed solid pharmaceutical dosage form, comprising:
    a) from about 60 to about 95% by weight acetaminophen in granular form;
    b) from about 1 to about 40% by weight of a direct compression vehicle comprising microcrystalline cellulose wherein said microcrystalline cellulose has been coprocessed with from about 0.1 to about 20% by weight silicon dioxide, whereby said microcrystalline cellulose and said silicon dioxide are in intimate association with each other;
    c) from about 0.1 to about 4% by weight of a pharmaceutically acceptable lubricant; said acetaminophen and said direct compression vehicle being combined under shear conditions sufficient to transform said acetaminophen and said direct compression vehicle into a homogeneous granulate without degradation, and which has been directly compressed into a solid pharmaceutical dosage form, said dosage form providing controlled release;
    d) from about 0.1 to about 5% by weight of a further amount of silicon dioxide.

2. The solid dosage form of claim 1, wherein said pharmaceutical dosage form comprises from about 60% to about 85% by weight acetaminophen.

3. The solid oral dosage form of claim 1, wherein said further amount of silicon dioxide is present in an amount from about 0.15% to about 0.9% by weight of the dosage form.

4. The solid oral dosage form of claim 1, wherein said further amount of silicon dioxide is present in amount from about 0.4 to about 0.75% by weight of the dosage form.

5. The solid oral dosage form of claim 1, wherein said silicon dioxide is derived from colloidal silicon dioxide.

6. The solid dosage form of claim 1, wherein said silicon dioxide coprocessed with said microcrystalline cellulose is present in an amount of from about 0.5 to about 10% by weight, based on the weight of said microcrystalline cellulose.

7. The solid dosage form of claim 1, wherein said silicon dioxide coprocessed with said microcrystalline cellulose is present in an amount of from about 1.25 to about 5% by weight, based on the weight of said microcrystalline cellulose.

8. The solid dosage form of claim 1, wherein said lubricant is sodium stearyl fumarate.

9. The solid dosage form of claim 1, wherein said lubricant is present in an amount from about 0.1 to about 1% by weight.

10. The solid dosage form of claim 1, wherein said lubricant is present in an amount from about 0.2 to about 0.45% by weight.

11. The solid dosage form of claim 9, wherein said lubricant has been combined with said acetaminophen and said direct compression vehicle under high shear conditions.

12. The solid dosage form according to claim 1, wherein the mixing under high shear conditions is performed with a mixer having an impeller and a chopper.

13. The solid dosage form of claim 1, further comprising a disintegrant.

14. The solid dosage form of claim 13, wherein said disintegrant has been combined with said acetaminophen and said direct compression vehicle under said high shear conditions.

15. A method of preparing a direct compressed solid pharmaceutical dosage form, comprising:
   a) coprocessing microcrystalline cellulose in the form of a wet cake with silicon dioxide to form an excipient, said microcrystalline cellulose and silicon dioxide being in intimate association with each other,
   b) drying said excipient;
   c) mixing said excipient with from about 60 to about 95% by weight acetaminophen in granular form under high shear conditions sufficient to transform said acetaminophen and said excipient into a first homogeneous granulate;
   d) combining said first homogeneous granulate with from about 0.1 to about 4.0% of a pharmaceutically acceptable lubricant under high shear conditions; and
   e) compressing said homogenous granulate containing said lubricant into a solid controlled release pharmaceutical dosage form.

16. The method of claim 15, wherein said pharmaceutical dosage form comprises from about 60% to about 85% by weight acetaminophen.

17. The method of claim 15, wherein the microcrystalline cellulose is coprocessed with about 0.1 to about 20% by weight of colloidal silicon dioxide and a further amount of silicon dioxide is added to the dosage form.

18. A method of effecting analgesia in mammals, comprising administering to a mammal in need of such analgesia a controlled release direct compressed dosage form containing:
   a) from about 60 to about 95% by weight acetaminophen in granular form;
   b) from about 1 to about 40% by weight of a direct compression vehicle comprising microcrystalline cellulose, wherein said microcrystalline cellulose has been coprocessed with from about 0.1 to about 20% by weight silicon dioxide, whereby said microcrystalline cellulose and said silicon dioxide are in intimate association with each other;
   c) from about 0.1 to about 4.0% of a pharmaceutically acceptable lubricant; and
   d) from about 0.1 to about 5% by weight of a further amount of silicon dioxide;
   said acetaminophen and said direct compression vehicle being combined under shear conditions sufficient to transform said acetaminophen and said direct compression vehicle into a homogeneous granulate without degradation which provides controlled release of said acetaminophen.

19. The method of preparing a direct compressed solid pharmaceutical dosage form of claim 15, wherein said lubricant is selected from the group consisting of sodium stearyl fumarate, magnesium stearate, hydrogenated vegetable oil, stearic acid, or polyethylene glycol (PEG).

20. The method of preparing a direct compressed solid pharmaceutical dosage of claim 15, wherein said lubricant is sodium stearyl fumarate.

21. The method of claim 15, wherein said silicon dioxide is colloidal silicon dioxide.

22. The method of preparing a direct compressed solid pharmaceutical dosage form of claim 1, wherein said lubricant is present in the amount from about 0.1 to about 1% by weight of the dosage form.

23. The method of preparing a direct compressed solid pharmaceutical dosage form of claim 15, wherein said lubricant is present in the amount from about 0.2 to about 0.45% by weight of the dosage form.

24. The method of preparing a direct compressed solid pharmaceutical dosage form, comprising the steps of:
   (a) combining at least 60% by weight acetaminophen, and from about 1 to about 40% by weight of a direct compression vehicle comprising microcrystalline cellulose, under dry shear conditions sufficient to transform said acetaminophen and said direct compression vehicle into a homogenous granulate without degradation; wherein said microcrystalline cellulose bas been coprocessed with from about 0.1 to about 20% by weight silicon dioxide, whereby said microcrystalline cellulose and said silicon dioxide are in intimate association with each other;
   (b) combining the homogenous granulate of step (a) with from about 0.1 to about 4.0% by weight of a pharmaceutically acceptable lubricant under high shear conditions; and
   (c) compressing the homogeneous granulate containing said lubricant into a solid pharmaceutical dosage form.

25. The method according to claim 15, wherein the mixing under high shear conditions is performed with a mixer having an impeller and a chopper.

26. The method according to claim 24, wherein the mixing under high shear conditions is performed with a mixer having an impeller and a chopper.

27. The method of claim 25, wherein said high shear mixing conditions used to combine said lubricant are less than said shear conditions used to form said first homogeneous granulate.

28. The method of claim 26, wherein said high shear mixing conditions used to combine said lubricant are less than said shear conditions used to form said first homogeneous granulate.

29. The method of claim 24, wherein a further amount of silicon dioxide is present in an amount from about 0.1 to about 5% by weight of the dosage form.

30. The method of claim 24, wherein said silicon dioxide is derived from colloidal silicon dioxide.

31. The method of claim 24, wherein said lubricant is sodium stearyl fumarate.

32. The solid dosage form of claim 1, further comprising a coating of a hydrophobic polymer.

33. The solid dosage form of claim 32, wherein the solid dosage form includes a sufficient amount of the hydrophobic polymer coating to provide a sustained release of the active agent over a predetermined period.

34. The solid dosage form of claim 32, wherein the coating further includes an enteric coating material.

35. The solid dosage form of claim 1, further comprising a coating of an enteric coating material.

36. The solid dosage form of claim 35, wherein the enteric coating material is selected from a group consisting of cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures thereof.

37. The solid dosage form of claim 32, wherein the coating further includes a hydrophilic material.

38. The solid dosage form of claim 1, further comprising a coating of a hydrophilic material.

39. The solid dosage form of claim 35, wherein the solid dosage form includes a sufficient amount of the coating to provide a sustained release of the active agent over a predetermined period.

40. The solid dosage form of claim 33, wherein the predetermined period is 12 hours.

41. The solid dosage form of claim 33, wherein the predetermined period is 24 hours.

42. The solid dosage form of claim 38, wherein the hydrophilic material is hydroxypropylmethylcellulose.

43. The solid dosage form of claim 1, further comprising a coating of an additional amount of the active agent.

44. The solid dosage form of claim 32, wherein the coating further includes an additional amount of the active agent.

45. The solid dosage form of claim 1, further comprising at least a partial coating of a support platform.

46. The solid dosage form of claim 38, wherein the solid dosage form includes a sufficient amount of the coating to provide a sustained release of the active agent over a predetermined period.

47. The solid dosage form of claim 46, wherein the predetermined period is 12 hours.

48. The solid dosage form of claim 46, wherein the predetermined period is 24 hours.

49. The solid dosage form of claim 35, wherein the coating further includes an additional amount of the active agent.

* * * * *